N. Patent

[19] Welter et al.

[11] Patent Number: 4,774,252
[45] Date of Patent: Sep. 27, 1988

[54] BENZISOSELENAZOLONYL DERIVATIVES AND PROCESSES FOR THE TREATMENT OF RHEUMATIC DISEASE

[75] Inventors: André Welter, Beyne-Hevsay; Christian Lambert, Visé, both of Belgium; Norbert Dereu, Frechen-Bachem, Fed. Rep. of Germany; Andrea Hüther, Cologne, Fed. Rep. of Germany; Eugen Etschenberg, Cologne, Fed. Rep. of Germany

[73] Assignee: A. Nattermann & Cie GmbH, Cologne, Fed. Rep. of Germany

[21] Appl. No.: 159,509

[22] Filed: Feb. 17, 1988

Related U.S. Application Data

[63] Continuation of Ser. No. 849,474, Apr. 8, 1986, abandoned.

[30] Foreign Application Priority Data

Apr. 27, 1985 [DE] Fed. Rep. of Germany ....... 3515273
Apr. 27, 1985 [DE] Fed. Rep. of Germany ....... 3515274

[51] Int. Cl.$^4$ .................. C07D 293/12; A61K 31/41
[52] U.S. Cl. .................. 514/359; 548/120; 548/121
[58] Field of Search .................. 548/121, 120; 514/359

[56] References Cited

U.S. PATENT DOCUMENTS 4,352,799 10/1982 Renson et al. ........................ 424/244
4,418,069 11/1983 Welter et al. ........................ 424/269
4,454,068 6/1984 Welter et al. ........................ 260/239 R
4,550,168 10/1985 Welter et al. ........................ 546/270

FOREIGN PATENT DOCUMENTS 3027074 2/1982 Fed. Rep. of Germany ...... 548/121
3407511 9/1985 Fed. Rep. of Germany ...... 548/121

OTHER PUBLICATIONS

S. Leyck, E. Etschenberg, U. Hadding, J. Winkelmann, Agents and Actions, 13, pp. 437–438 (1983).
W. Kraus and P. Oehm, Das Deutsche Gesundheitswesen, 1979, 34(37), 1713–1718, and 1979, 34(37), 1769–1773.
W. R. Gaythwaite, J. Kenyon and H. Phillips, J. Chem. Soc. (1928), 2280.

Primary Examiner—Robert Gerstl
Attorney, Agent, or Firm—Pearne, Gordon, McCoy & Granger

[57] ABSTRACT

The present invention relates to new benzisoselenazolonyl derivatives of the general formula (I)

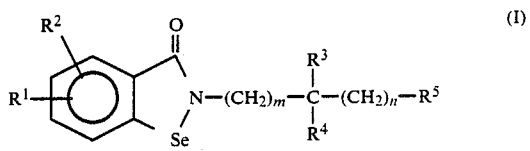

and processes for the treatment of rheumatic diseases.

8 Claims, No Drawings

BENZISOSELENAZOLONYL DERIVATIVES AND PROCESSES FOR THE TREATMENT OF RHEUMATIC DISEASE

This is a continuation of application Ser. No. 849,474, filed on Apr. 8, 1986, now abandoned.

The present invention relates to new benzisoselenazolonyl derivatives and a process for the treatment of rheumatic diseases.

Benzisoselenazolones having anti-arteriosclerotic and inflammation-inhibiting properties have been described repeatedly, for example in DE-OS No. 30 27 073=U.S. Pat. No. 4,352,799; DE-OS No. 30 27 075=U.S. Pat. No. 4,418,069; DE-OS No. 32 26 284=U.S. Pat. No. 4,550,168; DE-OS No. 32 26 286=U.S. Pat. No. 4,454,068.

It has now been found that benzisoselenazolonyl derivatives of the general formula (I)

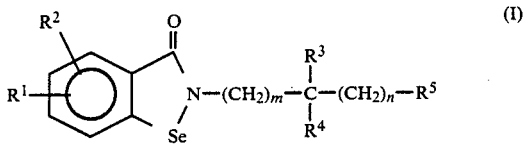

wherein:

$R^1$ and $R^2$ are identical or different and independently represent hydrogen, halogen, $C_{1-4}$-alkyl, $C_{1-4}$-alkoxy, trifluoromethyl, nitro or together mean methylenedioxy, $R^3$ is hydrogen, straight or branched $C_{1-4}$-alkyl, mercapto-$C_{1-2}$-alkyl, methylthio-$C_{1-2}$-alkyl or phenylmethyl, $R^4$ is hydrogen or methyl, $R^5$ is hydrogen, methyl, $C_{3-8}$-cycloalkyl, —COOH, —CONH$_2$, —CN or —COOR$^6$, R$^6$ being a straight or branched $C_{1-4}$-alkyl group, and m, n are identical or different and are zero or an integer of 1–8, wherein the alkylene chain —(CH$_2$)$_n$— with n=6 can also be present as a 1,4-cyclohexylene group, exhibit valuable pharmacological properties.

Preferred are benzisoselenazolonyl derivatives of the formula (I), wherein $R^1$, $R^2$ are identical or different and independently represent hydrogen, fluorine, chlorine, bromine, methyl, methoxy, trifluoromethyl, nitro or together mean methylenedioxy, $R^3$ represents hydrogen, straight or branched $C_{1-4}$-alkyl, mercapto-$C_{1-2}$-alkyl, methylthio-$C_{1-2}$-alkyl or phenylmethyl, $R^4$ represents hydrogen or methyl, $R^5$ represents —COOH and m and n represents zero.

Particularly preferred are compounds wherein $R^3$, $R^4$ both represent methyl, $R^5$ represents hydrogen or methyl and m and n represent zero.

The compounds of the formula (I) which can have a chirality center at the corresponding carbon atom due to different substituents for $R^3$ and $R^4$ can be present as racemates or in form of the D- or L-enantiomers according to the nature of the used starting substances. If a separation of the racemates is desired, it is conveniently carried out according to processes known per se by using suitable optically active bases via the formation of diastereomeric salts or by chromatography on an optically active column material.

Examples for the compounds of the present invention are as follows:

1,2-benzisoselenazole-3(2H)-one-2-yl acetic acid
1,2-bensisoselenazole-3(2H)-one-2-yl acetic acid methylester
L-2-(1,2-benzisoselenazole-3(2H)-one-2-yl)-propionic acid
L-2-(1,2-benzisoselenazole-3(2H)-one 2-yl)-propionic acid amide
L-2-(6-chloro-1,2-benzisoselenazole-3(2H)-one-2-yl)-propionic acid
L-2-(6-fluoro-1,2-benzisoselenazole-3(2H)-one-2-yl)-propionic acid
L-2-(6-methyl-1,2-benzisoselenazole-3(2H)-one-2-yl)-propionic acid
L-2-(6-trifluoro-methyl-1,2-benzisoselenazole-3(2H)-one-2-yl)propionic acid
L-2-(7-nitro-1,2-benzisoselenazole-3(2H)-one-2-yl)-propionic acid
L-2-(7-methoxy-1,2-benzisoselenazole-3(2H)-one-2-yl)-propionic acid
L-2-(6,7-methylenedioxy-1,2-benzisoselenazole-3(2H)-one-2-yl)-propionic acid
2-(1,2-benzisoselenazole-3(2H)-one-2-yl)-2-methylpropionic acid
2-(7-methoxy-1,2-benzisoselenazole-3(2H)-one-2-yl)-2-methylpropionic acid
3-(1,2-benzisoselenazole-3(2H)-one-2-yl)-propionic acid
4-(1,2-benzisoselenazole-3(2H)-one-2-yl)-butyric acid
L-2-(1,2-benzisoselenazole-3(2H)-one-2-yl)-3-methylthiopropionic acid
L-2-(1,2-benzisoselenazole-3(2H)-one-2-yl)-4-methylthiobutyric acid
DL-2-(1,2-benzisoselenazole-3(2H)-one-2-yl)-3-phenylpropionic acid
L-2-(1,2-benzisoselenazole-3(2H)-one-2-yl)-3-methylbutyric acid
DL-2-(1,2-benzisoselenazole-3(2H)-one-2-yl)-3-methylbutyric acid
L-2-(1,2-benzisoselenazole-3(2H)-one-2-yl)-4-methylvalerianic acid
5-(1,2-benzisoselenazole-3(2H)-one-2-yl)-valerianic acid
6-(1,2-benzisoselenazole-3(2H)-one-2-yl)-capronic acid
8-(1,2-benzisoselenazole-3(2H)-one-2-yl)-octanoic acid
10-(1,2-benzisoselenazole-3(2H)-one-2-yl)-decanoic acid
12-(1,2-benzisoselenazole-3(2H)-one-2-yl)-dodecanoic acid
14-(1,2-benzisoselenazole-3(2H)-one-2-yl)tetradecanoic acid
16-(1,2-benzisoselenazole-3(2H)-one-2-yl)-hexadecanoic acid
18-(1,2-benzisoselenazole-3(2H)-one-2-yl)-octadecanoic acid trans-4-(1,2-benzisoselenazole-3(2H)-one-2-ylmethyl)-cyclohexane carboxylic acid
1,2-benzisoselenazole-3(2H)-one-2-yl-acetonitrile
2-cyclopropylmethyl-1,2-benzisoselenazole-3(2H)-one
2-cyclohexylmethyl-1,2-benzisoselenazole-3(2H)-one
2-tert-butyl-7-methyl-1,2-benzisoselenazole-3(2H)-one
2-cyclohexylmethyl-6-fluoro-1,2-benzisoselenazole-3(2H)-one
2-cyclohexylmethyl-7-methoxy-1,2-benzisoselenazole-3(2H)-one
2-cycloheptylmethyl-1,2-benzisoselenazole-3(2H)-one
2-tert-butyl-6-chloro-1,2-benzisoselenazole-3(2H)-one
5-chloro-2-octyl-1,2-benzisoselenazole-3(2H)-one
2-tert-butyl-5-nitro-1,2-benzisoselenazole-3(2H)-one
2-cycloheptylmethyl-6,7-methylenedioxy-1,2-benzisoselenazole-3(2H)-one
2-pentyl-1,2-benzisoselenazole-3(2H)-one 2-hexyl-1,2-benzisoselenazole-3(2H)-one
2-octyl-1,2-benzisoselenazole-3(2H)-one
2-decyl-1,2-benzisoselenazole-3(2H)-one
2-dodecyl-1,2-benzisoselenazole-3(2H)-one
2-hexadecyl-1,2-benzisoselenazole-3(2H)-one
2-octadecyl-1,2-benzisoselenazole-3(2H)-one
2-tert-butyl-1,2-benzisoselenazole-3(2H)-one
2-isopropyl-1,2-benzisoselenazole-3(2H)-one
2-tert-butyl-7-nitro-1,2-benzisoselenazole-3(2H)-one
2-isopropyl-7-trifluoromethyl-1,2-benzisoselenazole-3(2H)-one.

The compounds of the present invention of the formula (I) have valuable pharmacological properties. To prove the imflammation-inhibiting activity, the Cobra-Venom-Factor (CVF)-oedema was selected, since it is known that substances which inhibit cyclooxygenase together with lipoxygenase, such as phenidone, as well as immunoregulating compounds, such as levamisole, show more significant inhibiting effect in CVF-oedema-test as in carragenine-test (S. Leyck, E. Etschenberg, U. Hadding, J. Winkelmann, Agents and Actions 13, 437–438 (1983)). The CVF-oedema is dependent from the activiation of the complement system which plays an important role in acute and chronic inflammation processes wherein it affects the activity of immuno complexes. Effectiveness in this test is quite representative for the usefulness of the tested compound in the therapy of many rheumatic dieseases. Particularly surprising is the degree of superior activity of the instant compounds in comparison to the reference substance ebselen, INN (1-phenyl-1,2-benzisoselenazolyl-3(2H)-one).

| Substance | $ED_{50}$ (mg/kg p.o.) |
|---|---|
| Ebselen (reference substance) | 56,2 |
| D,L-2-(1,2-benzisoselenazole-3(2H)—one-2-yl)-3-methyl butyric acid | 5,0 |
| 2-isopropyl-1,2-benzisoselenazole-3(2H)—one | 10,3 |
| 2-tert-butyl-1,2-benzisoselenazole-3(2H)—one | 17,7 |

$ED_{50}$ (mg/kg p.o.) values in CVF-oedema

The compounds of the present invention of formula (I) can be used for the treatment of numerous diseases, such as for prophylaxis and in therapy of infection diseases, for the stimulation of the immuno system or in selenium deficiency diseases as defined by W. Kraus and P. Oehm, Das Deutsche Gesundheitswesen, 1979, 34(37), 1713–1718, and 1979, 34(37), 1769–1773.

The benzisoselenazolonyl derivatives of the formula (I) however are in particular characterized by anti-arteriosclerotic and inflammation-inhibiting properties. In particular, they are suited in the therapy of rheumatic diseases such as arthrosis or chronic polyarthritis, in liver therapy, for the treatment of skin diseases like psoriasis. The new compounds are characterized by a very good compatibility since they are non-toxic and, contrary to the known inflammation-inhibiting therapeutics, they do not show any ulcus formation or gastro-intestinal irritations.

The compounds of the present invention are prepared according to processes known per se. o-Chloroselenobenzoic acid chlorides of the general formula (II)

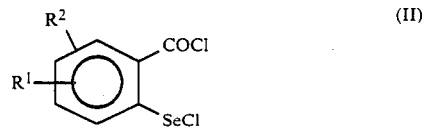

wherein $R^1$, $R^2$ have the meanings given in formula (I) are reacted with the amino group of compounds of the formula (III)

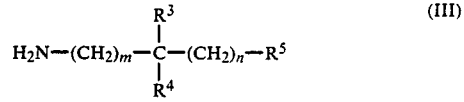

wherein $R^3$, $R^4$, $R^5$ have the meanings given in formula (I) under ring-closure conditions to form the benzisoselenazolonyl derivatives of the formula (I). Reactive groups in the compounds of formula (III) (f.i. a free carboxylic acid) have previously been protected in usual manner.

Particularly preferred is a process for the preparation of compounds according to claims 1-2, wherein $R^5$ represents a carboxyl group which is characterized in that in a one-pot-process, the corresponding aminocarboxylic acids of formula (III) in a suitable solvent under reflux conditions are converted into the trimethylsilylesters which, after cooling to 0° C., by addition of the corresponding o-chloroselenobenzoic acid chloride and of the necessary amount of triethylamine are condensed to form the benzisoselenazolonyl alkanoic acid trimethylsilylesters, the trimethylsilyl ester group in the resulting compounds as protective group being finally split off in usual manners to yield the corresponding free carboxylic acids of formula (III) with $R^5$=—COOH, (f.i. a free carboxylic group).

The corresponding o-chloroselenobenzoic acid chlorides are prepared according to the process of A. Ruwet and M. Renson, Bull. Soc. Chim. Belg. 1966, 76, 157–163, and of W. R. Gaythwaite, J. Kenyon and H. Phillips, J. Chem. Soc. (1928), 2280.

As starting compounds of the formula (II), for example the following compounds can be used:
2-chloroseleno-4-chlorobenzoylchloride
2-chloroseleno-4-fluorobenzoylchloride
2-chloroseleno-4-bromobenzoylchloride
2-chloroseleno-4-methylbenzoylchloride
2-chloroseleno-4-methoxybenzoylchloride
2-chloroseleno-4-trifluoromethylbenzoylchloride
2-chloroseleno-5-chlorobenzoylchloride
2-chloroseleno-5-nitrobenzoylchloride
2-chloroseleno-3-methoxybenzoylchloride
2-chloroseleno-3-nitrobenzoylchloride
2-chloroseleno-3,4-methylenedioxybenzoylchloride The starting compounds of the formula (III) are known compounds, such as:
Aminoacetic acid, aminoacetic acid methylester, L-2-aminopropionic acid, D-2-aminopropionic acid, D,L-2-aminopropionic acid, DL-2-aminopropionic acid ethylester, DL-2-aminopropionic acid tert-butylester, L-2-aminopropionic acid amide, 2-amino-isobutyric acid, 3-aminopropionic acid, 3-aminopropionic acid methylester, 4-aminobutyric acid, 4-aminobutyric acid ethylester, DL-2-aminobutyric acid ethylester, L-2-amino-3-mercaptopropionic acid, L-2-amino-2-methylthiopropionic acid, L-2-amino-4-methylthio butyric acid, DL- 2-amino-3-phenylpropionic acid, L-2-amino-3-methyl butyric acid, L-2-amino-4-methyl valerianic acid, 5-aminovalerianic acid, 6-aminocapronic acid, 8-aminooctanoic acid, 10-aminodecanoic acid, 12-aminododecanoic acid, 14-aminotetradecanoic acid, 16-aminohexadecanoic acid, 18-aminooctadecanoic acid, trans-4-aminomethylcyclohexane carboxylic acid, aminoacetonitrile, aminomethyl cyclopropane, aminomethyl cyclohexane, aminomethyl cyclooctane, pentylamine, hexylamine, octylamine, decylamine, dodecylamine, hexadecylamine, octadecylamine, isopropylamine, tert-butylamine.

The present invention also refers to pharmaceutical preparations containing compounds of the formula (I). The pharmaceutical preparations of the present invention are those for the enteric like oral or rectal as well as the parenteric administration containing the pharmaceutically active compounds alone or together with a common pharmaceutically acceptable carrier. Conveniently, the pharmaceutical preparation of the active compound is present in form of single doses adapted to the desired administration, such as tablets, dragees, capsules, suppositories, granulates, solutions, emulsions or suspensions. The dosage of the substances normally lies between 10 and 1000 mg per day, preferably between 30 and 300 mg per day, and the administration can be made in a single dose or in a plurality of partial doses, preferably in two to three partial doses per day.

The preparation of the compounds of the present invention is illustrated in detail in the following examples.

The melting points indicated therein were measured using a Büchi 510-melting point measurement apparatus and are indicated in °C. and not corrected.

EXAMPLE 1

3-(1,2-Benzisoselenazole-3(2H)-one-2-yl)propionic acid

To a solution of 8.9 g (0.1 mole) of 3-aminopropionic acid in 200 ml of chloroform and 40 ml of acetonitrile (anhydrous) 10.86 g (0.1 mole) of chlorotrimethylsilane are added. The mixture is refluxed for 3 hours, then cooled to 0° C. After the addition of 22.7 g (0.09 mole) of o-chloroseleno-benzoic acid chloride 30.3 g (0.3 mole) of triethylamine are added dropwise while stirring. The stirring of the mixture is continued for 2 hours and finally washed with 200 ml of a 5% aqueous solution of citric acid and 200 ml of a 10% solution of sodiumhydrogencarbonate. After acidifying the aqueous phase with diluted hydrochloric acid the precipitate is sucked off and recrystallized from methanol.

Yield: 10.3 g (38% of the theory); m.p. 188°–190° C.

EXAMPLE 2

4-(1,2-Benzisoselenazole-3(2H)-one-2-yl)-butyric acid similar to example 1 from:
22.7 g of o-chloroselenobenzoic acid chloride
10.31 g of 4-aminobutyric acid
Yield: 9.97 g (35% of the theory); m.p. 142°–145° C.

EXAMPLE 3

6-(1,2-Benzisoselenazole-3(2H)-one-2-yl)-capronic acid similar to example 1 from:
22.7 g of o-chloroselenobenzoic acid chloride
13.1 g of 6-aminocapronic acid
Yield: 13.24 g (42.3% of the theory); m.p. 100°–103° C.

EXAMPLE 4

1,2-Benzisoselenazole-3(2H)-one-2-yl-acetic acid similar to example 1 from:
11.35 g of o-chloroselenobenzoic acid chloride
3.75 g of aminoacetic acid
Yield: 4.76 g (39.5% of the theory); m.p. 197°–200° C.

EXAMPLE 5 trans-4-(1,2-Benzisoselenazole-3(2H)-one-2-yl-methyl)-cyclo-hexane-carboxylic acid To a solution of 10 g (0.0636 mole) of trans-4-(aminomethyl)cyclohexane-carboxylic acid and 8 g (0.2 mole) of sodium hydroxide in 100 ml of water 16.2 g (0.0636 mole) of o-chloroseleno-benzoic acid chloride are added while cooling with ice. The mixture is further stirred overnight at room temperature. After acidifying with diluted hydrochlorid acid to pH 2 the precipitate is sucked off and purified on a silicagel column (eluent dichloromethane/methanol 9:1).

Yield: 6.2 g (28.8%); m.p. 199°–201° C.

EXAMPLE 6

8-(1,2-Benzisoselenazole-3(2H)-one-2-yl)-octanoic acid similar to example 1 from:
11.35 g of o-chloroselenobenzoic acid chloride
7.96 g of 8-aminooctanoic acid
Yield: 6 g (40%); m.p. 132°–135° C.

EXAMPLE 7

12-(1,2-benzisoselenazol-3(2H)-on-2-yl)-dodecanoic acid similar to example 1 from:
11.35 g of o-chloroselenobenzoic acid chloride
10.76 g of aminododecanoic acid
Yield: 8.18 g (46.3% of the theory); m.p. 104°–105° C.

EXAMPLE 8

DL-2-(1,2-Benzisoselenazol-3(2H)-one-2-yl)phenyl-3-propionic acid similar to example 1 from:
11.35 g of o-chloroselenobenzoic acid chloride
8.26 g of DL-phenylalanine
Yield: 4.47 g (31,9%); m.p. 165° C.

EXAMPLE 9

(1,2-Benzisoselenazole-3(2H)-one-2-yl)-acetic acid nitrile similar to example 1 from:
11.35 g of o-chloroselenobenzoic acid chloride
2.79 g of 8-aminoacetonitrile
Yield: 3.6 g (34%); m.p. 164°–167° C.

EXAMPLE 10

L-2-(1,2-Benzisoselenazole-3(2H)-one-2-yl)-propionic acid similar to example 1 from:
11.35 g of o-chloroselenobenzoic acid chloride
4.45 g of aminopropionic acid
Yield: 1.68 g (14%); m.p. 211°–215° C.

EXAMPLE 11

4-(7-Methyl-(1,2-benzisoselenoazole-3(2H)-one-2-yl)-butyric acid similar to example 1 from:
2.69 g of 2-chloroseleno-3-methylbenzoic acid chloride
1.03 g of 4-aminobutyric acid
Yield: 0.98 g (44.7%); m.p. 168°–170° C.

EXAMPLE 12 trans-4-(1,2-Benzisoselenazole-3(2H)-one-2-yl-methyl)-cyclohexane-carboxylic acid methylester To a solution of 4.09 g (0.02 mole) of trans-4-aminomethylcyclohexane-carboxylic acid methylester-hydrochloride and 4.96 g (0.06 mole) of sodium hydrogencarbonate in 150 ml of water at 5° C. 5 g (0.02 mole) of o-chloroselenobenzoic acid chloride dissolved in 100 ml of diisopropylether are added dropwise within 40 minutes. The formed precipitate is sucked off, washed with little diethylether and with water. The insoluble residue is recrystallised from ethanol/ether.
Yield: 2.6 g (37.2%); m.p. 138° C.

EXAMPLE 13

1,2-Benzisoselenazole-3(2H)-one-2-yl-acetic acid ethylester similar to example 12 from:
3.06 g of o-chloroselenobenzoic acid chloride
1.68 g of aminoacetic acid ethylester-hydrochloride
Yield: 1.48 g (43,2%); m.p. 123°–124° C.

EXAMPLE 14

2-(1,2-Benzisoselenazole-3(2H)-one-2-yl)2-methylpropionic acid similar to example 1 from:
4.54 g of 2-chloroselenobenzoic acid chloride
2.06 g of 2-amino-2-methylpropionic acid
Yield: 4 g (70% of the theory); m.p. 215° C.

EXAMPLE 15

DL-2-(1,2-Benzisoselenazole-3(2H)-one-2-yl)-3-methyl-butyric acid similar to example 1 from:
5.1 g of 2-chloroselenobenzoic acid chloride
2.5 g of D,L-valine
Yield: 4.8 g (80% of the theory); m.p. 177°–179° C.

EXAMPLE 16

L-2-(1,2-Benzisoselenazole-3(2H)-one-2-yl)-3-methyl-butyric acid similar to example 1 from:
5.1 g of 2-chloroselenobenzoic acid chloride
2.5 g of L-valine
Yield: 4.6 g (77.2% of the theory); m.p. 165° C.

EXAMPLE 17

D-2-(1,2-Benzisoselenazole-3(2H)-one-2-yl)3-methyl-butyric acid similar to example 1 from:
5.1 g of 2-chloroselenobenzoic acid chloride
2.5 g of D-valine
Yield: 4.8 g (80.5% of the theory); m.p. 164°–166° C.

EXAMPLE 18

L-2-(1,2-Benzisoselenazole-3(2H)-one-2-yl)-3-methyl-valerianic acid similar to example 1 from:
4.54 g of 2-chloroselenobenzoic acid chloride
2.62 g of 2-amino-3-methyl-valerianic acid
Yield: 2.6 g (42% of the theory); m.p. 158°–160° C.

EXAMPLE 19

L-2-(1,2-Benzisoselenazole-3(2H)-one-2-yl)-4-methyl-butyric acid similar to example 1 from:
10 g of 2-chloroselenobenzoic acid chloride
6.5 g of L-methionine
Yield: 1 g (13% of the theory); m.p. 171°–172° C.

EXAMPLE 20

2-Cyclohexylmethyl-1,2-benzisoselenazole-3(2H)-one 2.2 g (0,02 mole) of aminomethylcyclohexane and 3.93 g (0,04 mole) of triethylamine are dissolved in 30 ml of dichloromethane and while stirring and cooling with ice added dropwise to a solution of 4.93 g (0,02 mole) of o-chloroselenobenzoic acid chloride in 70 ml of dichloromethane in a nitrogen atmosphere. The solution is further stirred overnight at room temperature and then concentrated. To the residue water is added and brought to pH 2 by diluted hydrochloric acid. The insoluble solid is sucked off and twice recrystallized from ethanol/water.
Yield: 2.55 g (44.7% of the theory); m.p. 155°–156° C.

EXAMPLE 21

2-tert-Butyl-1,2-benzisoselenazole-3(2H)-one

To a solution of 1.46 g (0.02 mole) of tert-butylamine in 36.2 ml of 1.1N NaOH at 5° C. 5.08 g (0.02 mole) of o-chloroselenobenzoic acid chloride dissolved in 38 ml of diisopropylether are added dropwise within 1 hour. The formed precipitate is sucked off, washed with little diethylether and with water. The insoluble residue is recrystallized from tetrahydrofuran.
Yield: 2.2 g (44% of the theory); m.p. 153°–154° C.

EXAMPLE 22

2-Hexyl-1,2-benzisoselenazole-3(2H)-one similar to example 20 from:
10 g of 2-chloroselenobenzoic acid chloride
13 g of hexylamine
Yield: 5.78 g (51.6% of the theory); m.p. 90°–94° C.

EXAMPLE 23

2-Isopropyl-1,2-benzisoselenazole-3(2H)-one similar to example 21 from:
12.7 g of 2-chloroselenobenzoic acid chloride
2.95 g of isopropylamine
Yield: 5.5 g (45.8% of the theory); m.p. 105°–106° C.

EXAMPLE 24

2-Octyl-1,2-benzisoselenazole-3(2H)-one similar to example 21 from:
2.54 g of 2-chloroselenobenzoic acid chloride
1.29 g of octylamine
Yield: 1.46 g (46.9% of the theory); m.p. 65° C.

EXAMPLE 25

2-Dodecyl-1,2-benzisoselenazole-3(2H)-one similar to example 21 from:
2.54 g of 2-chloroselenobenzoic acid chloride
1.85 g of dodecylamine
Yield: 1.63 g (44.4% of the theory); m.p. 77°–79° C.

EXAMPLE 26

6-Chloro-2-tert-butyl-1,2-benzisoselenazole-3(2H)-one similar to example 21 from:
5.79 g of 2-chloroselenobenzoic acid chloride
1.46 g of tert-butylamine
Yield: 2.1 g (36.2% of the theory); m.p. 245°–247° C.

EXAMPLE 27

5-Chloro-2-octyl-1,2-benzisoselenazole-3(2H)-one similar to example 21 from:
5.79 g of 5-chloro-2-chloroselenobenzoic acid chloride
2.585 g of octylamine
Yield: 2.85 g (41.3% of the theory); m.p. 224°–226° C.

EXAMPLE 28

2-tert-Butyl-5-nitro-1,2-benzisoselenazole-3(2H)-one similar to example 21 from:
6.0 g of 2-chloroseleno-5-nitro-benzoic acid chloride
1.46 g of tert-butylamine
Yield: 2.46 g (44% of the theory); m.p. 210°–212° C.

EXAMPLE 29

2-tert-Butyl-7-methyl-1,2-benzisoselenazole-3(2H)-one similar to example 21 from:
5.79 g of 2-chloroseleno-3-methylbenzoic acid chloride
1.46 g of tert-butylamine
Yield: 2.58 g (44.6% of the theory); m.p. 202°–205° C.

EXAMPLE 30

2-tert-Butyl-7-nitro-1,2-benzisoselenazole-3(2H)-one similar to example 21 from:
6.0 g of 2-chloroseleno-3-nitrobenzoic acid chloride
1.46 g of tert-butylamine
Yield: 2.8 g (50.2% of the theory); m.p. 150° C.

What we claim is:

1. Benzisoselenazolonyl derivatives of the general formula (I)

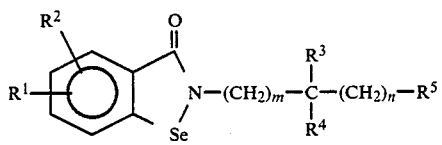

wherein:
R$^1$ and R$^2$ which may be identical or different from each other, represent members selected from the group consisting of hydrogen, halogen, C$_{1-4}$-alkyl, C$_{1-4}$-alkoxy, trifluoromethyl, nitro and, taken together, methylenedioxy,
R$^3$ is a member selected from the group consisting of hydrogen, straight C$_{1-4}$-alkyl, branched C$_{1-4}$-alkyl, mercapto-C$_{1-2}$-alkyl, methylthio-C$_{1-2}$-alkyl or phenylmethyl,
R$^4$ is a member selected from the group consisting of hydrogen and methyl,
R$^5$ is a member selected from the group consisting of C$_{3-8}$-cycloalkyl, —COOH, —CONH$_2$, —CN and —COOR$^6$, with R$^6$ being a member selected from the group consisting of a straight C$_{1-4}$-alkyl and branched C$_{1-4}$-alkyl and
m and n which may be identical or different from each other, are zero or an integer of from 1 to 8, wherein the alkylene chain —(CH$_2$)$_n$— with n=6 may also be present as a 1,4-cyclohexylene group.

2. Benzisoselenazolonyl derivatives of formula (I), according to claim 1, wherein:
R$^1$ and R$^2$ which may be identical or different from each other, are members selected from the group consisting of hydrogen, fluorine, chlorine, bromine, methyl, methoxy, trifluoromethyl, nitro and, taken together, methylenedioxy,
R$^3$ is a member selected from the group consisting of hydrogen, straight C$_{1-4}$-alkyl, branched C$_{1-4}$-alkyl, mercapto-C$_{1-2}$-alkyl, methylthio-C$_{1-2}$-alkyl and phenylmethyl,
R$^4$ is a member selected from the group consisting of hydrogen and methyl,
R$^5$ is a member selected from the group consisting of C$_{3-8}$-cycloalkyl, —COOH, —CONH$_2$, or —COOR$^6$, R$^6$ being a member selected from the group consisting of methyl, ethyl and tert-butyl group and
m and n which may be identical or different from each other, are zero or an integer of from 1 to 8.

3. Process for the treatment of rheumatic diseases in humans comprising administering to a human suffering from such a disease a compound of claim 1 in a daily dose of from 10 to 1000 mg per day in one or several partial doses per day.

4. Process for the treatment of rheumatic diseases in humans comprising administering to a human suffering from such a disease a compound of claim 2 in a daily dose of from 10 to 1000 mg per day in one or several partial doses per day.

5. Benzisoselenazolonyl derivatives of the general formula (I)

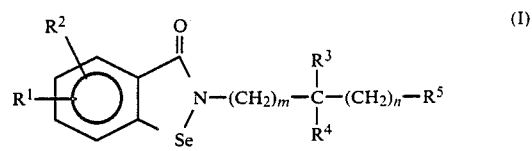

wherein:
R$^1$ and R$^2$ which may be identical or different from each other, represent members selected from the group consisting of hydrogen, halogen, C$_{1-4}$-alkyl, C$_{1-4}$-alkoxy, trifluoromethyl, nitro and, taken together, methylenedioxy,
R$^3$ is a member selected from the group consisting of straight C$_{1-4}$-alkyl, branched C$_{1-4}$-alkyl, mercapto-C$_{1-2}$-alkyl, methylthio-C$_{1-2}$-alkyl or phenylmethyl,
R$^4$ is methyl,
R$^5$ is a member selected from the group consisting of hydrogen, methyl, C$_{3-8}$-cycloalkyl, —COOH, —CONH$_2$, —CN and —COOR$^6$, with R$^6$ being a member selected from the group consisting of a straight C$_{1-4}$-alkyl and branched C$_{1-4}$-alkyl and
m and n which may be identical or different from each other, are zero or an integer of from 1 to 8, wherein the alkylene chain —$(CH_2)_n$— with n=6 may also be present as 1,4-cyclohexylene group.

6. Benzisoselenazolonyl derivatives of formula (I), according to claim 5, wherein:

$R^1$ and $R^2$ which may be identical or different from each other, are members selected from the group consisting of hydrogen, fluorine, chlorine, bromine, methyl, methoxy, trifluoromethyl, nitro and, taken together, methylenedioxy, $R^3$ is a member selected from the group consisting of straight $C_{1-4}$-alkyl, branched $C_{1-4}$-alkyl, mercapto-$C_{1-2}$-alkyl, methylthio-$C_{1-2}$-alkyl and phenylmethyl, $R^4$ is methyl, $R^5$ is a member selected from the group consisting of hydrogen, methyl, $C_{3-8}$-cycloalkyl, —COOH, —$CONH_2$, or —$COOR^6$, $R^6$ being a member selected from the group consisting of methyl, ethyl and tert-butyl group and m and n which may be identical or different from each other, are zero or an integer of from 1 to 8.

7. Process for the treatment of rheumatic diseases in humans comprising administering to a human suffering from such a disease a compound of claim 5 in a daily dose of from 10 to 1000 mg per day in one or several partial doses per day.

8. Process for the treatment of rheumatic diseases in humans comprising administering to a human suffering from such a disease a compound of claim 6 in a daily dose of from 10 to 1000 mg per day in one or several partial doses per day.

* * * * *